United States Patent [19]

Afeyan et al.

[11] Patent Number: 5,234,586

[45] Date of Patent: Aug. 10, 1993

[54] ON-LINE PRODUCT IDENTIFICATION IN A CHROMATOGRAPHY EFFLUENT BY SUBTRACTION

[75] Inventors: Noubar B. Afeyan, Brookline, Mass.; Fred E. Regnier, West Lafayette, Ind.

[73] Assignee: PerSeptive Biosystems, Inc., Cambridge, Mass.

[21] Appl. No.: 5,877

[22] Filed: Jan. 15, 1993

Related U.S. Application Data

[63] Continuation of Ser. No. 676,872, Mar. 28, 1991, abandoned.

[51] Int. Cl.$^5$ .................................. B01D 15/08
[52] U.S. Cl. .................... 210/198.2; 210/656; 73/61.52; 73/61.55; 73/61.56; 73/61.58; 422/70
[58] Field of Search ............ 210/85, 93, 198.2, 635, 210/656; 73/61.52, 61.55, 61.56, 61.58; 436/161, 162; 422/70

[56] References Cited

U.S. PATENT DOCUMENTS

| | | | |
|---|---|---|---|
| 3,676,649 | 7/1972 | Burk | 73/61.52 |
| 3,686,117 | 8/1972 | Lauer | 210/198.2 |
| 3,981,179 | 9/1976 | Root | 210/198.2 |
| 4,243,753 | 1/1981 | Regnier | 210/656 |
| 4,274,967 | 6/1981 | Snyder | 210/198.2 |
| 4,364,263 | 12/1982 | Sankoorikal | 210/198.2 |
| 4,403,503 | 9/1983 | Banerjee | 210/198.2 |
| 4,478,713 | 10/1984 | Girot | 210/198.2 |
| 4,544,485 | 10/1985 | Pinkerton | 210/656 |
| 4,577,492 | 3/1986 | Holba | 210/198.2 |
| 4,579,663 | 4/1986 | Poile | 210/198.2 |
| 4,592,842 | 6/1986 | Tomlinson | 210/198.2 |
| 4,724,081 | 2/1988 | Kawahara | 210/569 |
| 4,762,617 | 8/1988 | Stevens | 210/198.2 |
| 4,935,145 | 6/1990 | Cortes | 210/198.2 |
| 4,952,126 | 8/1980 | Hanaoka | 210/198.2 |
| 5,004,547 | 4/1991 | Grunfeld | 210/656 |
| 5,071,547 | 12/1991 | Cazer | 210/659 |

FOREIGN PATENT DOCUMENTS

| | | | |
|---|---|---|---|
| 61-212759 | 9/1986 | Japan | 73/61.58 |
| 64-15652 | 1/1989 | Japan | 73/61.52 |
| 1-191055 | 8/1989 | Japan | 73/61.52 |

OTHER PUBLICATIONS

Mikes Laboratory Handbook of Chromatographic and Allied Methods 1979, Ellis Horwood Limited, pp. 385–387.
Snyder, Introduction to Modern Liquid Chromatography, John Wiley & Sons, Inc., New York, pp. 130–131, 139–140, 410–416, 532–533 & 720–731.
Hearn (1987) *J. Chromatograph*, 418:3–26.
Regnier, (1987), *J. Chromatograph*, 418:115–143.
Karger et al., (1989), *Journal of Chromatography*, 492:585–614.
Knox et al., (1989), *Journal of Liquid Chromatography*, 12(13): 2435–2470.
Afeyan, et al., (1990) *Bio/Technology* 8:203–206.
Chicz, et al., (1990), *Methods in Enzymology*, vol. 182:392–421.
Foret, et al., (1990), *Electrophoresis*, 11:661–664.
Hoffstetter-Kuhn, et al., (1990), *Electrophoresis*, 11:304–309.
Novotny, et al., (1990), *Electrophoresis*, 11:735–749.

*Primary Examiner*—Ernest G. Therkorn
*Attorney, Agent, or Firm*—Testa, Hurwitz & Thibeault

[57] ABSTRACT

Disclosed is a method and apparatus for the rapid identification of a solute of interest in an effluent stream. The method involves separation of the solutes in the effluent and identification of a particular solute of interest by its selective subtraction from the effluent stream.

13 Claims, 4 Drawing Sheets

ON-LINE PRODUCT IDENTIFICATION IN A CHROMATOGRAPHY EFFLUENT BY SUBTRACTION

This is a continuation of copending application Ser. No. 07/676,872 filed on Mar. 28, 1991, now abandoned.

The present invention is generally related to a method and apparatus useful in chromatographic procedures. More particularly, this invention relates to a method for rapidly identifying products in a chromatography effluent.

BACKGROUND OF THE INVENTION

Chromatographic and electrophoretic techniques are well known in the art as means for separating components (solutes) present in a mixture. These techniques are particularly useful in the chemical and biotechnological arts. True chromatography describes the separation of solutes according to their different partitioning between two (or three) phases. The phases generally are solid and liquid, and solute partitioning results in their differing mobilities through a layer of solid particles (matrix) in the presence of a flowing phase. Solute transfer through the layer may be along a pressure gradient, generally referred to as "liquid chromatography". In contrast, electrophoretic systems separate solutes on the basis of their electrophoretic mobility, isoelectric point, and/or differential migration through a size discriminating matrix. Solute transfer in these systems is driven by a voltage gradient from an applied electric field, e.g., "electrophoresis".

Chromatographic matrices can separate components by any of a number of criteria, including size, electrical charge, hydrophobic interactions and/or specific affinity for the matrix or binding sites thereon. Because the components in the mixture will vary in their affinity for the matrix, their partitioning as they pass through the matrix separates the components so that they exit the matrix sequentially, separated temporally and spacially. Determination of the location of the various separated components, or of a given component of interest within the sequence, generally is achieved by collecting the fluid phase exiting the matrix (effluent stream) as a series of fractions and sampling these fractions to identify their contents by any of a number of means known in the art.

Resolution of the various components in the mixture depends on several considerations, chief among them being the partitioning ability of the matrix and the system's theoretical plate height and plate number (see infra). In general, a large surface area-to-volume ratio is desired. Matrices for liquid chromatography systems typically are housed in cylindrical chromatography systems known as columns. In electrophoresis systems, high resolution also demands efficient removal of the heat generated by the applied electric field. Capillary electrophoresis, or other electrophoretic modules which provide a large surface area-to-volume ratio, dissipate Joule heat well, allowing rapid analysis without significant loss of resolution.

The need to monitor a product's status during its synthesis or purification is well known in the art. Status monitoring is particularly important in multi-step preparative protocols. Frequently, the identity and, often, quality of a product in a mixture must be determined at each step. Product monitoring also may be used as part of a feedback system to adjust process parameters. Generally, identification is determined using a previously established criterion for identification, for example, a characteristic absorbance measured at a given wavelength. If the product of interest is a protein, identification also may be by molecular weight, activity, and/or immunoaffinity.

Unfortunately, product and/or process monitoring may be undesirably time-consuming, particularly when multiple samplings are required, as during a multi-step preparation. The time limitation of monitoring is of particular concern in industrial or other large scale preparations. To be useful, the monitor step should be rapid, adaptable, and repeatable. Accordingly, there exists a need for a method of rapidly identifying the presence and location of a molecule of interest during any preparative protocol.

It is therefore an object of this invention to provide a method and apparatus for the rapid, on-line identification of molecular products during a preparative protocol, such as during their synthesis or purification. Another object is to provide a method and apparatus for rapidly identifying the presence and location of a solute in a chromatography effluent. Another object is to provide a method for rapidly detecting the concentration of a product in an effluent stream. Still another object is to provide a method for rapidly assessing the success of a purification or separation protocol. These and other objects and features of the invention will be apparent from the drawing, description, and claims which follow.

SUMMARY OF THE INVENTION

A method and apparatus now has been discovered for rapidly identifying the presence and location of a preselected solute or subset of solutes in an effluent stream. The method and apparatus are particularly useful as part of a monitoring system during a preparative protocol. As used herein, "differential migration separation systems" (DMSS) is understood to include all methods known in the art for separating solutes present in a mixture, including those known as "liquid chromatography" and "electrophoresis."

The method of this invention comprises the steps of first passing a mixture through a system capable of separating the components in the mixture (solutes) so that they are separated temporally and spatially to some degree as they exit the system in a fluid phase (effluent stream). In preferred embodiments of the invention, this first system is a liquid chromatography matrix, e.g., a column, or other means for separating solutes, such as an electrophoresis module. The effluent stream from this first solute separation system (referred to herein as "first effluent stream"), then is passed through a detector to produce a first output describing the sequence of the solutes exiting the column. Identification of a particular solute of interest within this sequence of solutes is determined by passing this first effluent stream through a second system capable of selectively extracting the solute of interest from the fluid phase. Except for its ability to extract the solute of interest, this second system should be substantially inert, so that the sequence of solutes is essentially unaltered as the fluid phase passes through the second system, except that it will be substantially depleted in the component of interest. Preferably, the selective extraction occurs by some form of specific binding interactions between the matrix and the solute of interest. Particularly useful selective extraction systems include use of immunoadsorbents and immunoaffinity matrices.

The effluent stream exiting the second system then is passed through a detector to produce a second output which describes the sequence of the components exiting the second system. Because the second system selectively extracts the component of interest without significantly altering the temporal and/or spatial arrangement of the other solutes in the effluent stream, the difference between the first and second outputs can be used to determine the location in the effluent stream of the product of interest. Thus, the component of interest may be missing or depleted in the second output. Accordingly, a comparison of the two outputs will identify the location of the solute of interest in the first effluent stream.

The detectors used may be any means for molecule detection commonly used in the art. Currently preferred detectors include apparatus capable of monitoring the U.V. absorbance of a liquid, such as a spectrophotometer. In addition, both the first and second outputs may be produced by a single detector or, alternatively, by separate detectors. Similarly, the first and second outputs may be compared visually or electronically. Electronic comparison may include subtraction of the second output from the first output to produce a third output presenting only the presence and location of the component of interest in the first effluent stream. The detector also may comprise means for calculating and displaying the concentration of the solute of interest in the first effluent stream. In addition, the component of interest bound to the second system subsequently may be eluted, detected and quantified as a means of confirming the data generated by subtraction. Finally, the apparatus of this invention may be integrated into an automated purification or other preparative system, to act as a product and/or process monitor, and the various steps involved in performing the method of the invention placed under computer control.

The method and apparatus of this invention are rapid, reliable, and adaptable. The method of this invention is particularly useful in the preparation of biological macromolecules, particularly in the separation and purification of proteins. It will be understood by those skilled in the art that in a particularly useful aspect of the invention, the first and second systems may be readily regenerated with recycling solvents, allowing the systems to be used repeatedly throughout a given procedure.

The method and apparatus of this invention also may be used to identify multiple components in an effluent stream, by passing different samples of the first effluent stream through different second systems capable of selectively extracting different solutes of interest and comparing the outputs from these systems with the first output.

The method of this invention also may be used to assess the purity of a solute of interest. Because the second system is designed to selectively extract the solute of interest from the first effluent stream, the presence of any contaminants that coelute with the solute of interest in the first effluent stream will be indicated in the second effluent stream.

In still another embodiment of the invention, the method and apparatus disclosed herein may be used as part of an on-line process monitoring system to assess process conditions in real time, with the information generated used to alter conditions as needed to optimize production. For example, coeluting solutes identified by overlapping peaks in a monitoring output on-line may be separated by altering particular process conditions such as, for example, a buffer pH or the parameters of an elution gradient.

DETAILED DESCRIPTION

Figure 1:
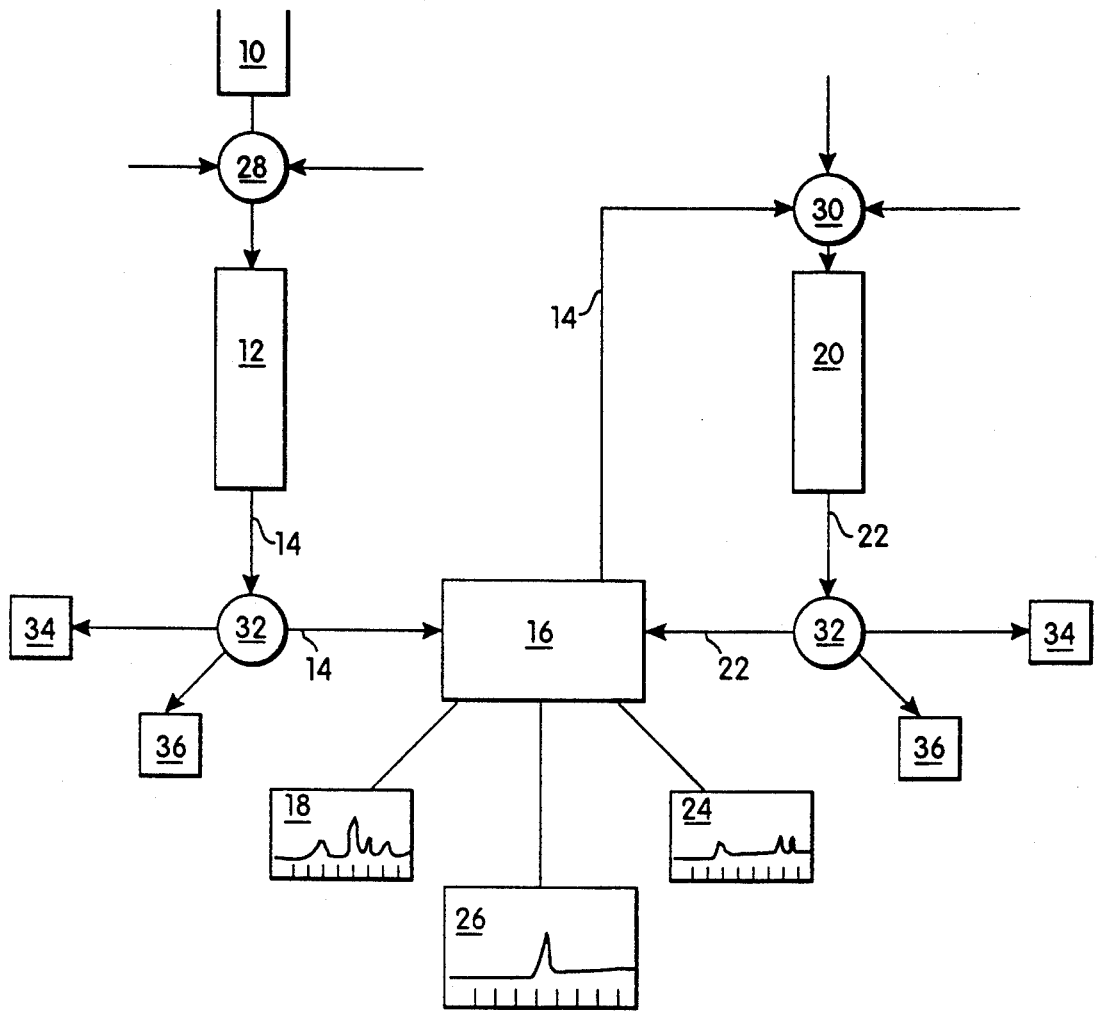
FIG. 1 is a schematic representation of one embodiment of the apparatus of this invention.

The method and apparatus of this invention may be understood by referring to the schematic representation of one embodiment of the invention, depicted in FIG. 1. A sample 10 containing the mixture to be separated is provided to a first system 12 capable of partitioning the components of the mixture (solutes). The effluent stream 14 from this first system containing the separated solutes then is passed through a detector 16 to produce a first output 18 which describes the temporal and/or spatial sequence of the mixture components exiting the first system. The effluent stream 14 then is passed through a second system 20 capable of selectively extracting a solute of interest from the first effluent stream 14. The temporal and spatial sequence of the solutes in a second effluent stream 22 will be substantially identical to that of the first effluent stream, provided that the second system is of an appropriate geometry and is sufficiently inert such that all but the component of interest pass through the system without significant interaction or delay.

The effluent stream 22 exiting the second system 20 then is passed through the detector 16 to produce a second output 24 describing the temporal and/or spatial sequence of the solutes remaining in the effluent. The detector also may subtract the second output 24 from the first output 18 to produce a third output 26 describing only the presence and position of the solute of interest in the first effluent stream 14. The detector also may have means for determining the concentration of the solute of interest in the first effluent stream, and means for displaying this data. Finally, the bound solute may be subsequently eluted from the second system, detected, and quantified to confirm the substraction data. Where the solute of interest is a protein, a typical detector is a conventional detector which measures U.V. absorbance through a film of fluid.

The apparatus may be used as part of a monitoring system within a molecule preparation system, which may be automated. In this case the apparatus preferably further comprises a multi-port sampling valve 28 such as is found in automated protein production systems known to those skilled in the art. The multi-port sampling valve may provide samples to the first system 12, as well as all necessary solvents or buffers, including washing solvents, eluting solvents, "running" solvents for electrophoresis systems, and recycling solvents to regenerate the system as needed between samplings. Similarly, a multi-port sampling valve 30 provides fluids to the second system, including the first effluent stream and all necessary solvents. Valve position for both multi-port valves preferably is under computer control, and fluid delivery may be driven by a metering pump. The multi-port valves further may include "stream splitters" or other means for reducing and/or directing only the desired flow rate to the first and second systems. Valves 32 at the exit of both the first and second systems direct the fluids exiting the systems to the detector 16, to waste collectors 34, or to product collectors 36. If desired, means also may be provided for recycling the detected samples. It will be understood by those skilled in the art that, where the first and/or second system is an electrophoretic module, means for providing the necessary applied electric fields also will be provided and may be under computer control.

As part of a process monitoring system, the method of this invention may be useful in assessing and/or developing a particular separation or purification protocol. For example, in an ion exchange chromatography system, variations in pH significantly affect solute separation. Using the method of the present invention one can rapidly assess the effect of various pH values on solute separation on-line, and alter appropriate conditions to optimize separation. In preferred embodiments of the invention, this assessment can be performed rapidly using minute sample quantities. Accordingly, the method allows on-line production optimization without substantial loss of sample or time.

As part of a product monitoring system, the method of this invention also may be useful in identifying the presence of contaminants that coelute with the solute of interest. Provided that the second system selectively extracts essentially all of the solute of interest from the fluid phase without significantly affecting the quantity or position of the remaining solutes in the sample mixture, the presence of a solute in the second output a the position generally occupied by the solute of interest can indicate the presence of a contaminant. Moreover, identification can be corroborated by eluting the solute of interest, quantifying it and comparing this value with that for the pertinent peaks in the first and second outputs.

Among the key features of this invention which make it useful as part of a product and/or process monitoring protocol are the speed, quality, and reliability of solute identification. This requires rapid fluid transfer through both systems in the apparatus, and no significant loss of resolution between the first and second effluent streams.

Resolution of partitioned solutes in a mixture is a function of both the affinity of the various solutes for the partitioning component (generally a matrix) and the theoretical plate height of the system. A "plate" in column chromatography can be considered to be the largest uniform zone able to accommodate a solute. The smaller the plate height of a column, the more discrete steps (higher plate number) a solute will encounter traveling through the matrix, providing better separation between similar components. Generally, the greater the matrix surface area-to-column volume ratio, the smaller the plate height and larger the plate number achievable. Column design generally focuses on designing the smallest matrix volume possible that provides a sufficient plate number to resolve components of interest. Smaller volumes increase the speed of fluid transfer through the system and reduce zone spreading. Preferred matrices are those composed of porous particles, as these provide a substantially greater surface area-to-volume ratio than a packed matrix of solid (non-porous) particles.

One particularly useful differential migration separation system in use today is the HPLC system (high performance liquid chromatography). HPLC columns utilize matrices of homogenous porous small bead particles. Because the dense packing of these small beads creates a high resistance to liquid flow, the equipment is designed to operate at high pressures, which allows rapid fluid transfer. The densely packed particles create a large surface area-to-volume ratio which works well resolving small molecular weight solutes. However, conventional HPLC systems are substantially less successful when used to resolve large molecular weight solutes such as proteins. Flowthrough speed of large molecular weight solutes such as proteins through a conventional HPLC matrix becomes limiting, primarily because mass transfer within the particle pores becomes diffusive, as compared to the mass transfer between pores, which is convective. While one can increase flow rates at the expense of high pressure drops, this tends to reduce separation quality.

These limitations of conventional HPLC analysis are overcome by the use of high speed chromatographic matrices capable of perfusive chromatography. These matrices comprise particles which may be of the same overall size as are sometimes employed in conventional matrices, but having increased intraparticle porosity. In addition to intraparticle throughpores of increased diameter, e.g., 6000–8000 Å, particles capable of perfusive chromatography have a network of 500–1500 Å pores interconnecting the larger throughpores. The resulting network limits the diffusional path lengths within the particles so that mass transfer within the particle pores over a large fluid velocity range is governed essentially by convection. The effect is to permit increase of the mobile phase velocity of these systems to greater than 10–100 times that of conventional HPLC systems (greater than 1000 cm/hr), with no substantial loss in resolution. A more detailed description of perfusive chromatography is provided in U.S. application Ser. No. 376,885, filed Jul. 6, 1989 and Afeyan et al. (1990) *Bio/Technology* 8:203–206, the disclosures of which are hereby incorporated by reference. Perfusive chromatography matrix materials are available commercially from PerSeptive Biosystems, Inc., of Cambridge, Mass. U.S.A. The increased porosity of particles capable of perfusive chromatography substantially increases the available surface area of the column, typically to levels within the range of about 30–50 $m^2$/ml, greatly reducing column plate height. Accordingly, miniscule columns (microcolumns) may be used and analysis may be performed at heretofore unattainable speeds with no significant loss of resolution.

Perfusive matrices are currently preferred liquid chromatography matrices for both the first and second system in the apparatus of this invention. Perfusive matrices for use in the first system, designed to partition and resolve components of a mixture, may be derivatized as desired using conventional methods known to those of ordinary skill in the art, to create a particular chromatography system. For example, the matrix may partition solutes by size, or be derivatized to separate solutes by charge (e.g., act as ion or anion exchangers), by metal ion affinity, or by hydrophobicity or hydrophilicity. Other useful matrices include inorganic substances such as calcium phosphate (hydroxyapatite), bentonite, alumina, and titanium or zinc oxide gels.

Another method for separating solutes in solution and particularly useful in the method o this invention is electrophoresis. Capillary electrophoresis, in particular, provides the appropriate geometry (high surface area-to-volume ratio) needed to dissipate the Joule heat generated by high applied electric fields. By tolerating these high applied fields, the capillary electrophoresis system, like perfusive HPLC, allows rapid throughput without loss of resolution. In addition, the capillary geometry can achieve the necessary plate number in a small volume, allowing the system to be run as a microcolumn. Accordingly, as with perfusive HPLC systems, capillary electrophoretic systems allow significant sample size reductions and rapid analysis.

Electrophoresis can separate molecules by a number of different modes, and these all may be performed in a capillary system. Among the most useful modes are zone or "free-flow" ("open") electrophoresis, gel electrophoresis and isoelectric focusing. Zone electrophoresis is characterized by an absence of solid supports and separation is within a single phase (e.g., liquid). Nonetheless, the separation record in zone electrophoresis, particularly capillary zone electrophoresis, still resembles the record obtained for standard elution chromatography and the formal concepts of plate number and resolution as defined for column chromatography are widely accepted.

In general, any electrophoretic system, including conventional polyacrylamide "slab" gels, may be used, provided the limitations that zone broadening imposes on the system (e.g., caused by diffusion, Joule heat and/or changes in conductivity) are understood and minimized. For example, isoelectric focusing and zone electrophoresis systems having channel thicknesses less than about 200 μm generally are considered useful for the method and apparatus of this invention. Further information on electrophoretic theory, applications, instrumentation and automation, including capillary electrophoresis, can be found in a number of sources known to those of ordinary skill in the art. Particularly useful sources include Karger et al., (1989) *J. Chromatogr.* 492:585-614; Foret et al., (1990) *Electrophoresis* 11:661-664; and Novotny et al. (1990) *Electrophoresis* 11:735-749.

As stated above, the second system should not significantly affect the position or concentration of the solutes remaining in solution. This means that the geometry of the system is important. The minimum volume that will adequately bind substantially all of the solute of interest should be used. In addition, non-specific binding must be minimized to prevent false negatives. Preferably, non-specific adsorption should be less than about 1 ng/10 ul. Accordingly, the binding surface or matrix should be substantially inert, capable of selectively extracting the solute or solutes of interest, preferably quantitatively, without significantly altering the resolution of the solutes remaining in the effluent. If desired, non-specific binding may be further minimized in the second system by first coating the potential non-specific binding sites with a nonspecific molecule, before loading the sample. It will be understood by those skilled in the art that this "coat" molecule should bind sufficiently under elution conditions so as not to interfere with the output of the second effluent stream.

Currently preferred matrices for selectively extracting the solute of interest are those capable of specific binding interactions with the solute. Most preferably, these interactions are reversible, and the system may be regenerated by means of one or more recycling solvents capable of dissociating the solute from the column, and preparing the system for another sample. Useful solute-specific binding sites include immunoadsorbents (e.g., antibodies) and other proteins capable of interacting specifically with the solute of interest. For example, one can envision the solute and solute-specific binding site comprising any ligand/enzyme combination, including hormones, toxins, lectins and their appropriate receptors. Where the solute of interest is an enzyme, the binding site may comprise a pseudo-substrate or an inhibitor. In general, the solute-specific binding site (solute-specific affinity sorbent) can be any immobilized ligand that demonstrates a bioaffinity for the given eluent of interest. The matrix surface may be derivatized so that the solute-specific binding site is bound irreversibly to the matrix surface. The bound solute then may be eluted and the column regenerated for subsequent samples. Alternatively, the solute-specific binding site may be attached non-covalently to the matrix surface. This allows the system to be adapted for use with different target solutes. One particular solute-specific binding site may be removed from the system by means of one or more recycling solvents, and a second binding site, specific for a second, different solute, then applied to the system. For example, protein A or protein G may be covalently bound to the matrix surface, allowing multiple, different solute-specific antibodies to be bound to the matrix in turn.

The solute-specific matrix may be incorporated in a liquid chromatography system or in an electrophoretic system (e.g., capillary electrophoresis system). Alternatively, the solute-specific binding sites may be attached to the inner surface of a capillary tube, or any other surface capable of providing a sufficiently high surface area-to-volume ratio. Capillary chromatography then may be performed using a pressure gradient or a voltage gradient.

The invention may be further understood by the following, nonlimiting examples:

EXAMPLE 1

Figure 2A:
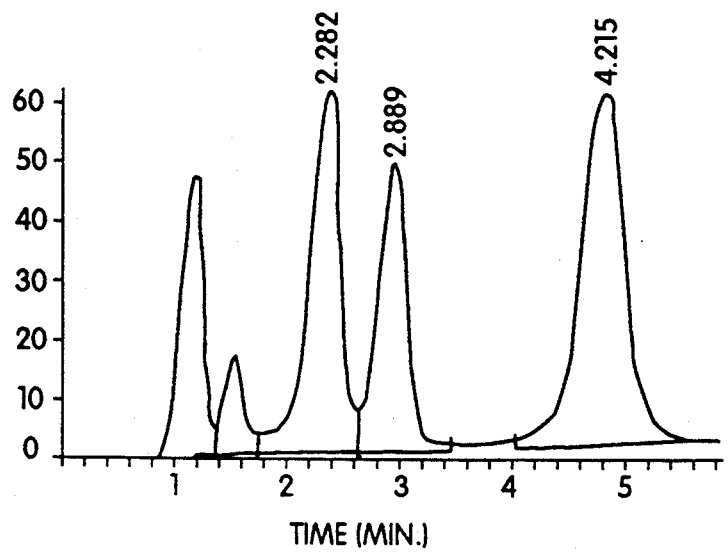
FIGS. 2A-2C represent elution curves based on absorbance at 280 nm for a first output (2A), and a second output (2B), wherein the solute of interest, HSA, is missing in the second output, and 2C represents the absorbance spectrum for the subsequently eluted HSA.

In this experiment, human serum albumin (HSA) is identified in a mixture. A first system is created using a perfusive ion exchange media (IEC, POROS SM, 4.6×50 mm column) to separate a mixture containing human serum albumin (HSA, 50 μg); chymotrypsin (CT, 25 μg); cytochrome C (Cyt, 25 μg); and lysozyme (Lys, 25 μg) in 1 ml of phosphate buffered saline (PBS). The mixture is loaded at 1 ml/min in PBS, and eluted at 1 ml/min with a gradient of 90% Buffer A (20 mM morpholine ethane sulfonic acid, pH 6.0)/10% Buffer B (20 mM MES, containing 1M NaCl) at t=0 minutes, and 50% Buffer A/50% Buffer B at t=8 minutes. The first effluent stream is detected with a spectrophotometer measuring absorbance at 280 nm. As can be seen in FIG. 2A, five peaks are identified in the first output.

Figure 2B:
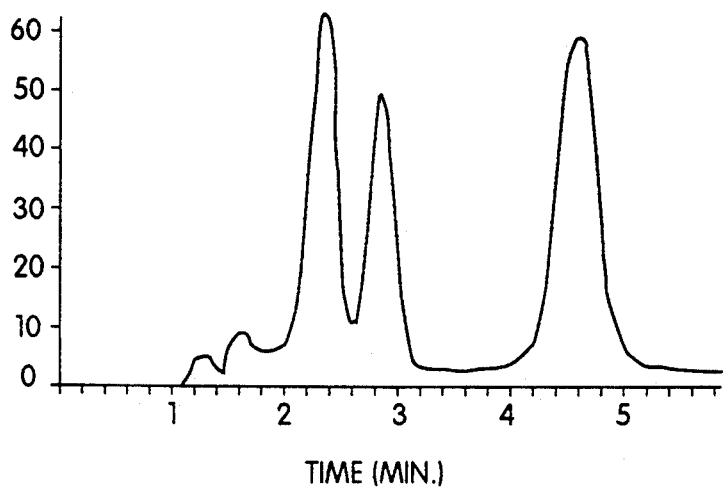
Figure 2C:
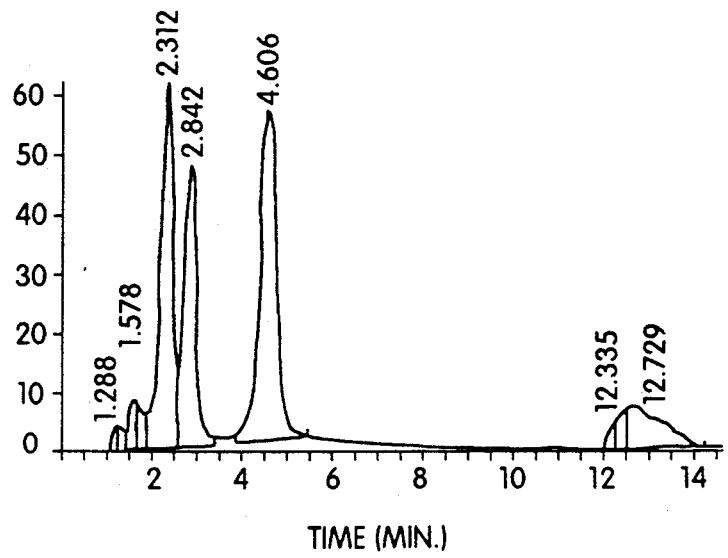

The first effluent stream then is passed through the second system which is placed in line after the IEC column. The second system is created with a perfusive reverse phase media (POROS RM, 2.1×30 mm) that has previously been loaded at 1 ml/min with a solution containing 170 μg purified anti-HSA (Sigma Co, Cincinnati, Ohio, No. A-2672) and 1.6 mg bovine serum albumin (BSA). BSA is added to essentially coat the unbound matrix surface, thereby substantially preventing non-specific binding of the sample with the matrix. As seen in FIG. 2B, when the first effluent stream is passed through the second system, at least 90% of peaks 1 and 2 is depleted, whereas peaks 3, 4 and 5 elute with their concentrations unaffected. Moreover, peaks 3, 4, and 5 elute from the second system at the same relative distance from one another as they did from the first system. As a check, the bound HSA then is eluted from the second system at 1 ml/min with a solution containing 2% acetic acid and 300 mM $MgCl_2$. As can be seen in FIG. 2C, this releases at least 90% of the bound HSA in a broad peak at approximately 13 min. For this and the subsequent experiments the characteristic outputs for each member of the mixture alone has previously been determined for the conditions of the given experiment. In this first example, then, it is known that, in the presence of PBS and at a flow rate of 1 ml/min., HSA elutes at about 1 min., CT at about 2.3 min., Cyt at about 2.9 min., and Lys at about 4.7 min. However, it should be clear from the Specification and Examples that this verification is not necessary in the method of this invention.

EXAMPLE 2

Figure 3A:
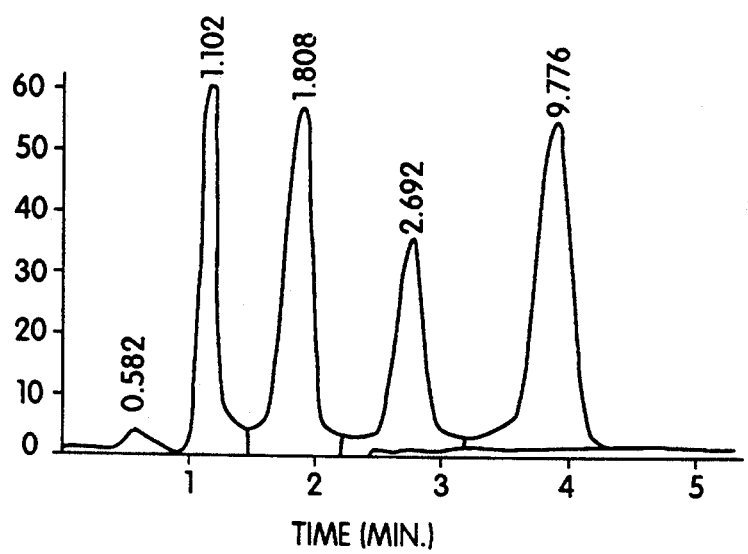
FIGS. 3A-3C represent elution curves based on absorbance at 280 nm for a first and second output (3A and 3B, respectively) and for HSA alone (3C)

A second method for identifying HSA is tested here. A sample containing 45 μg HSA, 22.5 μg CT, 22.5 μg Cyt and 22.5 Lys is passed through a first system containing a perfusive ion exchange media (POROS SM, 4.6×50 mm column) under the same conditions as for Example 1. The first output is shown in FIG. 3A. In this example, somewhat better separation is achieved and HSA appears to elute as a single peak (at 1.1 min). In addition, a small amount of protein appears in the void fraction at 0.58 min.

Figure 3B:
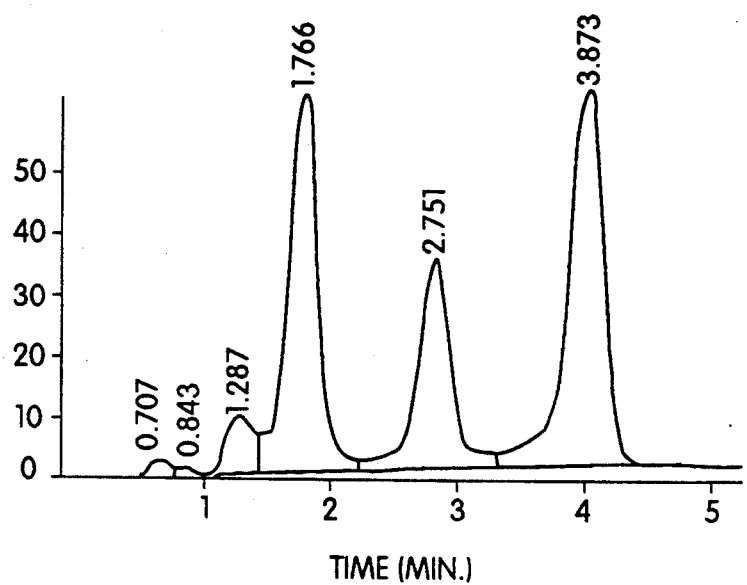

The first effluent then is passed through a second system in line after the POROS SM column. The second system is created with a perfusive protein G affinity column (POROS GM, 2.1×30 mm) which previously has been loaded at 0.5 ml/min with 2 ml PBS containing polyclonal goat anti-HSA (1 ml, Sigma Co., No. A-7544, 3.9 mg total antibody/1 ml). Elution is performed as for Example 1 and the second effluent then is detected at 280 nm, producing the output represented in FIG. 2B. A comparison of FIGS. 3A and 3B show that at least about 90% of the HSA present in the first effluent is captured by the second system without affecting the remaining solutes, unequivocally identifying the presence of HSA in the sequence.

Figure 3C:
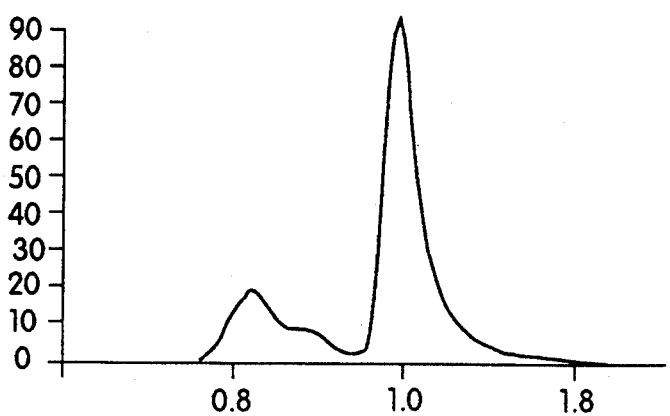

To determine if the protein in the void fraction in Example 2 is HSA, HSA is run over an IEC column alone, under the same conditions as described for Examples 1 and 2 (100 μg HSA in PBS, loaded in 20 μl). Elution with the standard Buffer A/Buffer B gradient described above produces both the void fraction peak at 0.58 min and HSA (at 1.1 min, see FIG. 3C). This chromatogram clearly shows that the protein in the void volume is a contaminant introduced with HSA.

EXAMPLE 3

In this example, IgG is the solute of interest and comprises a small portion of a crude cell extract supernatant mixture.

A first system, containing a perfusive anion exchange matrix (POROS QM, 4.6×100 mm column) is loaded with a 50 μl sample volume containing 50 μg IgG and a 100 fold excess of a hybridoma crude cell culture supernatant (5 mg protein). The sample is loaded at 5 ml/min and eluted at the same flow rate with a gradient of 100% Buffer C (20 mM Tris, O NaCl, pH 8)/0% Buffer D (Buffer C+1M NaCl) at t=0 minutes; and 0% Buffer C/100% Buffer D at t=10 minutes. The effluent is detected at 280 nm to produce the output represented in FIG. 4A.

Figure 4A:
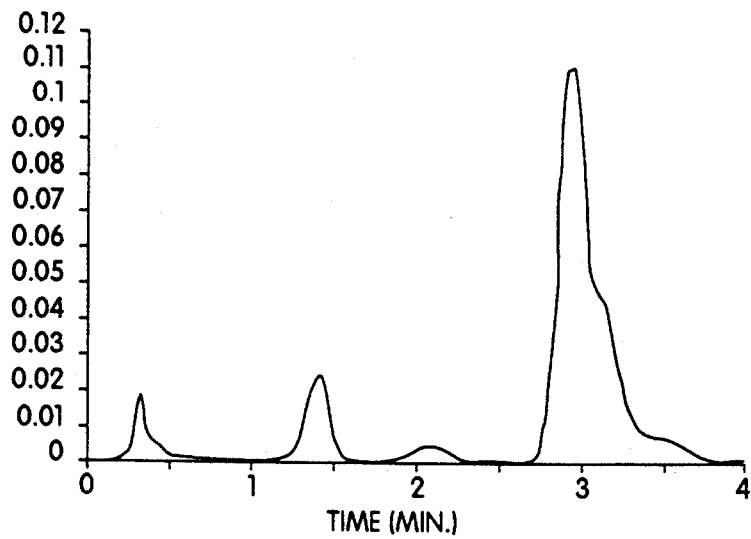
FIGS. 4A-4C represent elution curves based on absorbance at 280 nm for a first output (4A), and a second output (4B), and 4C is an overlay of these first and second outputs, showing the absence of the solute of interest, IgG, from second output.
Figure 4B:
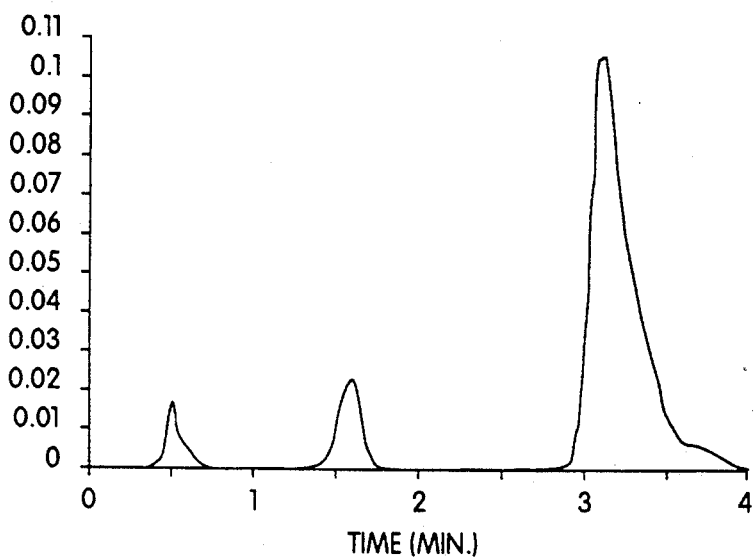
Figure 4C:
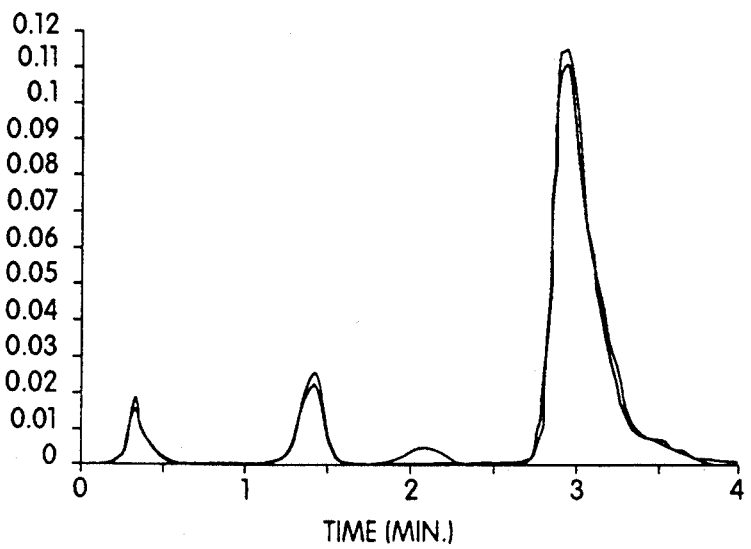

The effluent then is passed through a second system in line with the first system. The second system contains a perfusive Protein A affinity matrix (POROS AM, 4.6×50 mm column). The sample is run at 5 ml/min and this second effluent is detected at 280 nm to produce the output represented in FIGS. 4B. The third peak, IgG, at 2.1 min. is missing from the second output. An overlay of FIGS. 4A and 4B, represented in FIG. 4C, shows that the position of the remaining solutes is unchanged in the first and second effluents. IgG can be eluted from the column with a recycling solvent composed of 2% acetic acid, 0.3M $MgCl_2$ and 0.15M NaCl.

The invention may be embodied in other specific forms without departing from the spirit and central characteristics thereof. The present embodiments are therefore considered in all respects to be illustrative and not restrictive, the scope of the invention being indicated by the pended claims rather than by the foregoing description, and all changes which come within the meaning and range of equivalency of the claims are therefore intended to be embraced therein.

What is claimed is:

1. An apparatus for identifying a preselected subset of individual solutes from a liquid feed which includes a plurality of solutes, comprising:
    means for interacting differentially with said plurality of solutes in said liquid feed to produce a first stream rich sequentially in individual solutes;
    first detector means for providing a first output indicative of the temporal presence of said individual solutes in said first stream;
    means for extracting from said first stream said preselected subset of said individual solutes, said means comprising a solute specific affinity chromatography sorbent, to produce a second stream rich sequentially in remaining individual solutes;
    second detector means for providing a second output indicative of the temporal presence in said second stream of said remaining individual solutes; and
    comparator means which compares said first output and said second output and which identifies the presence and location of said preselected subset of said individual solutes in said first stream.

2. The apparatus of claim 1 wherein said first detector means and said second detector means comprise a single detector.

3. The apparatus of claim 1 wherein one of said detector means comprises means for monitoring the ultraviolet absorbance of solutes in a liquid passing through said one of said detector means.

4. The apparatus of claim 1 wherein said means for interacting differentially comprises a liquid chromatography system.

5. The apparatus of claim 4 wherein said liquid chromatography system comprises chromatography media selected from the group consisting of anionic exchange, cationic exchange, hydrophobic interaction, hydrophilic interaction, molecular sieve, size exclusion, metal ion affinity and bioaffinity media.

6. The apparatus of claim 1 wherein said means for interacting differentially with plural solutes in a liquid feed comprises an electrophoretic system.

7. The apparatus of claim 6 wherein said electrophoretic system is a capillary electrophoretic system.

8. The apparatus of claim 6 or 7 wherein said electrophoretic system is selected from the group consisting of gel electrophoresis, zone electrophoresis and isoelectric focusing.

9. The apparatus of claim 1 wherein said means for extracting comprises a solute-specific affinity sorbent for extracting a single solute.

10. The apparatus of claim 1 wherein said plural solutes in said liquid feed comprise biological macromolecules.

11. The apparatus of claim 1 wherein one of said detector means comprises means for detecting the presence of a protein in a liquid passing through said one of said detector means.

12. The apparatus of claim 1 wherein one of said detector means comprises means for detecting the instantaneous concentration of said individual solutes.

13. The apparatus of claim 1 wherein said means for interacting differentially comprises a liquid chromatography system comprising ionic exchange chromatography media.

* * * * *